United States Patent [19]

Sher et al.

[11] Patent Number: 5,491,134
[45] Date of Patent: Feb. 13, 1996

[54] SULFONIC, PHOSPHONIC OR PHOSPHINIIC ACID $\beta_3$ AGONIST DERIVATIVES

[75] Inventors: Philip M. Sher, Plainsboro; Arvind Mathur, Bridgewater, both of N.J.

[73] Assignee: Bristol-Myers Squibb Company, Princeton, N.J.

[21] Appl. No.: 307,217

[22] Filed: Sep. 16, 1994

[51] Int. Cl.⁶ ........................ A61K 31/66; A61K 31/185; C07F 9/30; C07F 9/38
[52] U.S. Cl. .......................... 514/114; 514/576; 514/577; 558/187; 562/11; 562/42
[58] Field of Search ............................... 558/187; 562/11, 562/42; 514/114, 576, 577

[56] References Cited

U.S. PATENT DOCUMENTS

| | | | |
|---|---|---|---|
| 3,723,524 | 3/1973 | Augstein et al. | 260/559 |
| 4,338,333 | 6/1982 | Ainsworth et al. | 424/309 |
| 4,707,497 | 11/1987 | Cecchi et al. | 514/647 |
| 4,772,631 | 9/1988 | Holloway et al. | 514/539 |
| 5,064,863 | 11/1991 | Alig et al. | 514/653 |
| 5,153,210 | 10/1992 | Ainsworth et al. | 514/369 |

FOREIGN PATENT DOCUMENTS

94/02493 7/1992 WIPO.
95/07284 3/1995 WIPO.

Primary Examiner—Johann Richter
Assistant Examiner—Michael G. Ambrose
Attorney, Agent, or Firm—Ellen K. Park

[57] ABSTRACT

Compounds of the formula $$R^1-A-CH(OH)-CH_2-NH-CH(R^2)-CH(B)(R^3)-C_6H_4-O-CH_2-R^4 \quad I$$

and pharmaceutically acceptable salts thereof wherein:

A is a bond or $-OCH_2-$, where the oxygen is linked to $R^1$;

B is $-CH_2-$ or when $R^3$ is hydrogen, B may be $-CH_2O-$ where the oxygen is linked to the phenyl ring;

$R^1$ is an aryl group;

$R^2$ is hydrogen or lower alkyl;

$R^3$ is hydrogen; or $R^2$ and $R^3$ together form the group $-CH_2CH_2-$; and $R^4$ is $-SO_3H$, $-P(O_2H)R^5$, $-P(O_2R^{5'})R^5$, $-PO_3H_2$, $-PO_3HR^{5'}$ or $-PO_3(R^{5'})_2$ where $R^5$ and $R^{5'}$ are independently lower alkyl. These compounds are beta$_3$ adrenergic receptor agonists and are useful, for example, in the treatment of diabetes, obesity, achalasia, and gastrointestinal diseases.

14 Claims, No Drawings

SULFONIC, PHOSPHONIC OR PHOSPHINIIC ACID β₃ AGONIST DERIVATIVES

BRIEF DESCRIPTION OF THE INVENTION

The present invention is directed to compounds of the formula

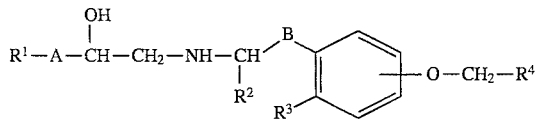

and pharmaceutically acceptable salts thereof. As used in formula I, and throughout the specification, the symbols have the following meanings:

A is a bond or —OCH₂—, where the oxygen is linked to R¹;

B is —CH₂— or when R³ is hydrogen, B may be —CH₂O— where the oxygen is linked to the phenyl ring;

R¹ is an aryl group;

R² is hydrogen or lower alkyl;

R³ is hydrogen; or R² and R³ together form the group —CH₂CH₂—; and

R⁴ is —SO₃H, —P(O₂H)R⁵, —P(O₂R⁵')R⁵, —PO₃H₂, —PO₃HR⁵' or —PO₃(R⁵')₂ where R⁵ and R⁵' are independently lower alkyl.

The compounds of formula I possess activity at the beta 3 adrenergic receptor in mammals and are useful in the treatment of diabetes, obesity, achalasia and intestinal hypermotility disorders.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the temps as they are used throughout the specification (unless they are otherwise limited in specific instances) either individually or as part of a larger group.

The term "alkyl" refers to both straight and branched chain groups having 1 to 12 carbon atoms, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

The term "lower alkyl" as employed herein includes such alkyl groups as described above containing 1 to 6 carbon atoms.

The term "alkoxy" refers to any of the above alkyl groups linked to an oxygen atom.

The term "lower alkoxy" refers to any of the above lower alkyl groups linked to an oxygen atom.

The term "aryl" refers to monocyclic or bicyclic aromatic groups containing from 6 to 10 carbons in the ring portion, such as phenyl or naphthyl; or such groups optionally substituted by one or more substituents selected from halogen, trifluoromethyl, alkyl, alkoxy, cycloalkyl, aryl, alkylsulfonylamino, nitro or alkylsulfonyl; or such groups optionally substituted by one or more reactive substituents such as cyano, hydroxy, hydroxymethyl, amino, aminocarbonyl or acylamino.

The term "halogen" or "halo" refers to chlorine, bromine, fluorine or iodine.

The compounds of formula I can be converted to salts, in particular pharmaceutically acceptable salts using any recognized procedures. The compounds of formula I have a basic center, and they can form acid addition salts. These are formed, for example, with strong inorganic acids, such as mineral acids for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as alkane- (of 1 to 4 carbon atoms) or arylsulfonic acids, for example methane- or p-toluenesulfonic acid. Corresponding acid addition salts can also be formed having, if desired, an additionally present basic center. The compounds of formula I having at least one acid group can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form.

It should be understood that the present invention includes prodrug forms of the compounds of formula I.

The compounds of the instant invention may be in the free or hydrate form, and may be obtained by methods exemplified by the following descriptions.

Compounds of formula I where R¹ contains no reactive substituents (reactive substituents include nucleophilic groups such as hydroxyl and electrophilic groups such as cyano) can be prepared by coupling a compound having the formula

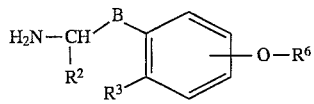

where R⁶ is methyl or benzyl with a compound of formula

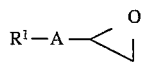

to provide a compound of formula

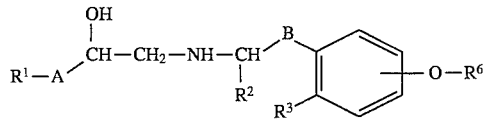

by heating II and III together optionally in the presence of a solvent or by the method described in R. K. Atkins et al., Tet. Lett., 27, 2451 (1986).

Compounds of formula IV are then reacted with a carbonylating agent such as 1,1'-carbonyldiimidazole in a solvent such as methylene chloride or tetrahydrofuran to form compounds of formula

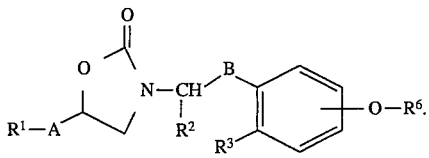

Compounds of formula V are then reacted with a Lewis acid such as boron tribromide in a solvent such ms methylene chloride or a protic acid such as aqueous HBr and acetic acid to form compounds of formula

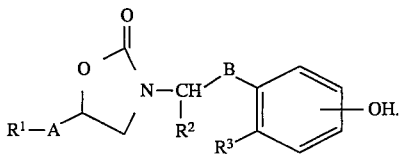

Where $R^6$ in formula V is benzyl, this step may also be accomplished by catalytic hydrogenation in a solvent such as ethanol, ethyl acetate or acetic acid in the presence of a catalyst such as palladium on carbon or palladium hydroxide on carbon.

The compounds of formula VI are then reacted with compounds of formula VII $XCH_2R^7$ where X is a suitable leaving group and $R^7$ is —$SO_3H$, —$PO_3(R^{7A})_2$, or —$P(O_2R^{7A})R^5$, where $R^{7A}$ is benzyl or a lower alkyl group. Suitable leaving groups include chlorine, bromine, iodine and oxygen leaving groups such as —$OSO_2CH_3$, —$OSO_2CF_3$, —$OSO_2C_6H_4Cl$ and —$OSO_2C_6H_4CH_3$. In the above reaction of compounds of formula VI and VII, where $R^7$ in formula VII is —$SO_3H$, the reaction may be carried out by the methods described in R. B. Petigara et al., *J. Het. Chem.*, 11, 331 (1974) and H. J. Barber et al., *J. Appl. Chem.*, 3, 253 (1953). For cases where $R^7$ is —$P(O_2R^{7A})R^5$, the compounds of formula VI and VII are reacted by the methods described in U.S. Pat. No. 4,536,355 and U.K. Patent 2146025B. Where $R^7$ is —$PO_3(R^{7A})_2$, the reaction is carried out similarly, for example, employing a base such as potassium carbonate, sodium hydroxide, or sodium hydride in a solvent such as tetrahydrofuran, acetone, dimethyl sulfoxide, or N,N-dimethylformamide. A study of this reaction in which X is varied is described in J. Comforth et al., *J. Chem. Soc. Perkin Trans.* 1, 1897 (1994 ).

The reaction of VI with VII provides compounds of formula

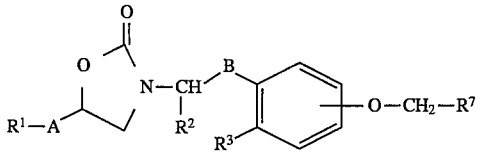

which are then hydrolyzed for example by heating in aqueous sodium hydroxide or lithium hydroxide optionally in the presence of a cosolvent such as ethanol or 1,4-dioxane or by the method described in P. G. Gassman et al., *J. Am. Chem. Soc.*, 98, 1275 (1976), to form the compounds of formula I where $R^4$ is —$SO_3H$, —$PO_3HR^{5'}$ (if $R^{7A}$ is lower alkyl), or —$P(O_2H)R^5$.

To form the compounds of formula I where $R^4$ is —$PO_3H_2$, the compounds of formula VIII, where $R^7$ is —$PO_3(R^{7A})_2$, are treated first with trimethylsilyl bromide or trimethylsilyl iodide or aqueous hydrohalic acid, or where $R^{7A}$ (see compound VII) is benzyl with hydrogen in the presence of a catalyst such as palladium on carbon, and then hydrolyzed as above. Alternatively, basic hydrolysis may be performed first.

Compounds of formula I where $R^1$ contains a reactive substituent such as hydroxyl may be prepared by following the procedures described above for reaction of compounds of formula II and III to form IV, conversion of IV to V to VI, reaction of VI with VII to form VIII, and hydrolysis of VIII to I, when a suitable protecting group for the reactive substituent is available. Such a protecting group would survive all of the reaction conditions through the formation of VIII, but it would be cleaved under the reaction conditions that provide I from VIII, namely strong basic hydrolysis. For example, the reactive substituent hydroxyl may be masked as p-toluenesulfonyloxy. Similarly, hydroxymethyl may be masked as 2,4,6-trimethylbenzoyloxymethyl. Other suitable masking groups may be found in Protective Groups in Organic Synthesis by T. W. Greene (John Wiley & Sons). Thus, the protected form of the reactive substituent is in place at the beginning of the synthesis such that compounds of formula

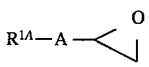

are utilized instead of III. In structure IIIA, $R^{1A}$ is defined as $R^1$ with the reactive substituent masked.

As an alternative, $R^{1A}$ may also represent $R^1$ with the reactive substituent in a precursor or protected form that is stable to the basic hydrolysis conditions that provide I from VIII, but which under other reaction conditions gives rise to the reactive substituent. In this scenario, compounds of formula IIIA lead ultimately to compounds of formula

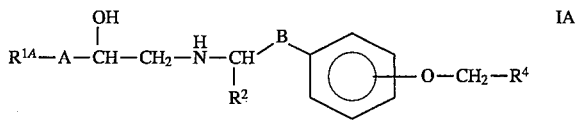

instead of I. Compounds of formula IA are then converted to I by one or more steps in which the reactive substituent is derived from its masked or precursor form. For example, to prepare the compounds of formula I in which $R^1$ is aminophenyl, compounds of formula IA where $R^{1A}$ is nitrophenyl are utilized and IA is converted to I by hydrogenation over Raney Nickel catalyst in a solvent such as ethanol or tetrahydrofuran. As another example, to prepare the compounds of formula I in which $R^1$ is hydroxyphenyl, compounds of formula IA where $R^{1A}$ is methoxyphenyl may be utilized and IA is convened to I by treatment with boron tribromide in methylene chloride.

To prepare the compounds of formula I in which $R^1$ is acylaminophenyl, compounds of formula IA where $R^{1A}$ is nitrophenyl are utilized and IA is converted to I by first converting the nitrophenyl group to an aminophenyl group as described above and then converting the aminophenyl group to an acylaminophenyl by treatment with an acyl chloride or the corresponding pentafluorophenyl ester in an acidic medium such as aqueous hydrochloric acid solution or an organic solvent, such as N,N-dimethylformamide, containing a strong acid, such as p-toluenesulfonic acid.

To prepare the compounds of formula I in which $R^1$ is cyanophenyl, $R^{1A}$ is bromophenyl or iodophenyl and IA is converted to I by radical cyanation, for example, by heating with tri-n-butyltin chloride, sodium cyanoborohydride, 2,2'-azobis(isobutyro-nitrile), and tert-butyl isocyanide in tert-butanol solution. Other methods for the conversion of IA to I, such as by treatment with potassium cyanide in the presence of a palladium catalyst, are found in the volumes of Compendium of Organic Synthetic Methods, Section 190 (John Wiley & Sons) and in D. M. Tschaen et al., *Synth. Comm.* 24, 887 (1994).

To prepare the compounds of formula I in which $R^1$ is aminocarbonylphenyl, compounds of formula IA where $R^{1A}$ is bromophenyl or iodophenyl are utilized and IA is converted to I by first converting the bromophenyl or iodophenyl group to a cyanophenyl group as described above and then converting the cyanophenyl group to an aminocarbonylphenyl by methods described in the volumes of Compendium of Organic Synthetic Methods, Section 88 (John Wiley & Sons), such as treatment with potassium hydroxide in tert-butanol or with aqueous hydrochloric acid solution.

An optional modification of the route described above for the formation of compounds of formula IV where A is a bond involves coupling the amine II with a compound of formula

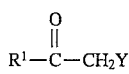  III' where Y is chlorine, bromine or iodine, rather than III. Subsequent ketone reduction then provides the compounds of formula IV. The methods used for coupling and ketone reduction and methods for the preparation of compounds III' are exemplified in R. H. Uloth et al., *J. Med. Chem.*, 9, 88 (1966) and A. A. Larson et al., *J. Med. Chem.*, 10, 462 (1967).

Another optional method for obtaining compounds of formula IV involves coupling of amine II with a compound of formula

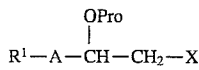  III"

where X is defined as above and Pro is a suitable protecting group such as triethylsilyl, optionally in the presence of an acid scavenger such as diisopropylethylamine and a solvent such as tetrahydrofuran, to form the compounds of formula

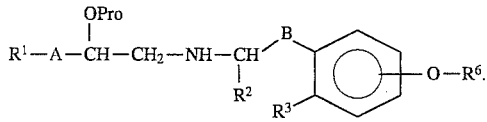  IV'

Compounds of formula IV' are then deprotected by treatment with a deprotecting agent, such as tetrabutylammonium fluoride in a solvent such as tetrahydrofuran to provide the compounds of formula IV.

Another optional modification of the routes described above for the formation of I, involves protection of the ethanolamine moiety of IV as the N-acetyl derivative of formula

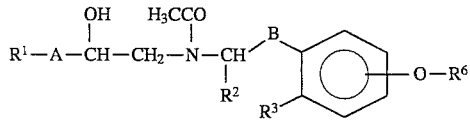  V' rather than as the oxazolidinone V. The compounds of formula V' are prepared from the compounds of formula IV by treatment with an acetylating agent such as acetic anhydride in a solvent such as methylene chloride in the presence of a scavenger base such as pyridine.

The subsequent synthetic steps are analogous to those described above for the conversion of V to VI to VIII to I except that compounds of formula V' are utilized in place of V to provide compounds of formula

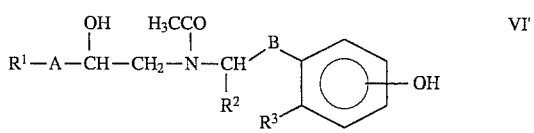  VI' which are then convened to compounds of formula

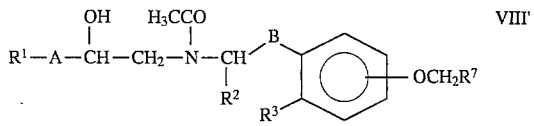  VIII' which are more easily hydrolyzed (than compounds of formula VIII) to provide the compounds of formula I.

The compounds of formula I where $R^4$ is $-PO_3(R^{5'})_2$ or $-P(O_2R^{5'})R^5$ are prepared from the compounds of formula I where $R^4$ is $-PO_3HR^{5'}$ or $P(O_2H)R^5$, respectively, by formation of the silver salt of the phosphorous acid, for example by treatment with silver nitrate or silver triflate in water or an alcohol solvent optionally in the presence of a base such as triethylamine, followed by alkylation with $R^{5'}I$, a lower alkyl iodide, such as ethyl iodide, in a solvent such as methylene chloride optionally in the presence of an acid such as p-toluenesulfonic acid. The same method may also be used to prepare the compounds of formula I where $R^4$ is $-PO_3(R^{5'})_2$ or $-PO_3HR^{5'}$ from those where $R^4$ is $-PO_3H_2$.

As an alternative to all of the above, the compounds of formula I where $R^4$ is $-PO_3H_2$, $-PO_3HR^{5'}$, or $-PO_3(R^{5'})_2$, B is $-CH_2-$, $R^3$ is hydrogen and the substituent $-O-CH_2-R^4$ on the aromatic ring is in the para position relative to the linker B, may be prepared by coupling compounds of formula III with compounds of formula

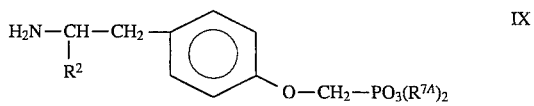  IX to form compounds of formula

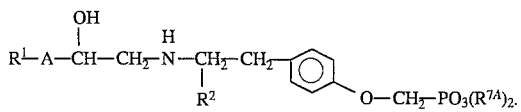  X

The compounds of formula X where the substituent $R^{7A}$ is a lower alkyl group, are the compounds of formula I where $R^4$ is $-PO_3(R^{5'})_2$. The methods described above for deesterification and reesterification of phosphonic acid derivatives may be applied to the compounds of formula X to provide compounds of formula I where $R^4$ is $-PO_3HR^{5'}$ or $-PO_3H_2$ and $-PO_3(R^{5'})_2$ if $R^{7A}$ is not the desired lower alkyl group, $R^{5'}$. Compounds of formula IX are available as described in WO 94/02493.

It is recognized that various permutations of optional synthetic modifications are possible. For example, use of a protecting group for a reactive substituent as in IIIA may be employed where the coupling agent is a haloketone as in III' or where the amino group is later masked as the N-acetyl derivative as in V'.

Compounds of formula II are commercially available or prepared by methods known in the art. For example the method described in D. E. Nichols et al., *J. Med. Chem.*, 16, 480 (1973), is used to prepare (in optically active form) the compounds of formula II where B is $-CH_2-$, $R^2$ is lower alkyl, $R^3$ is hydrogen, and $R^6$ is methyl. The compounds of formula II where B is $-CH_2-$, $R^2$ is either hydrogen or lower alkyl, $R^3$ is hydrogen, and $R^6$ is methyl are prepared by the method described in H. B. Hass et al., *J. Org. Chem.*, 15, 8 (1950). This method can also be used to prepare like analogs where $R^6$ is benzyl by substituting lithium aluminum hydride reduction for catalytic hydrogenation. All of the compounds of formula II where B is —$CH_2O$— are prepared by the methods described in A. Waefelaer et al., *Bull. Soc. Chim. Belg.*, 85, 421 (1976). The compounds of formula II where B is —$CH_2$—, $R^2$ and $R^3$ together are —$CH_2CH_2$—, and $R^6$ is methyl are prepared as described in Q. Ye et al., *J. Med. Chem.*, 32, 478 (1989). Those where $R^6$ is benzyl may be prepared employing the same methods, but substituting lithium aluminum hydride reduction for catalytic hydrogenation.

Compounds of formula III and IIIA in which A is a bond are commercially available or prepared by methods known in the art, for example the method described in M. Imuta et al., *J. Org. Chem.*, 44, 1351 (1979). These compounds may also be prepared in optically active form by the method described in E. N. Jacobsen et al., *J. Am. Chem. Soc.*, 113, 7063 (1991). Compounds of formula III and IIIA in which A is —$OCH_2$— are available in optically active form as described in J. M. Klunder et al., *J. Org. Chem.*, 54, 1295 (1989).

Compounds of formula III" where X is chlorine, bromine or iodine and where A is a bond are prepared in high enantiomeric purity from compounds of formula III' by treatment with borane using a solvent such as tetrahydrofuran with a chiral auxiliary by the method described in E. J. Corey et al., *J. Org. Chem.*, 56, 442 (1991) to generate compounds of formula

Subsequent treatment of compounds of formula XI with an alcohol protecting agent such as triethylsilyl chloride in a solvent such as pyridine generates the compounds of formula III" where X is chlorine, bromine or iodine and A is a bond. In this scheme, compounds of formula III" where X is iodine may also be prepared from compounds III' where X is bromine or chlorine by employing halogen exchange, such as with sodium iodide in acetone, prior to alcohol protection.

Compounds of formula III" where X is an oxygen atom leaving group such as triflate or p-toluenesulfonate may be prepared in high enantiomeric purity from compounds of formula XII

by the following steps: 1.) asymmetric dihydroxylation according to the methods of K. B. Sharpless et al., described in *J. Org. Chem.*, 57, 2768 (1992) 2.) primary alcohol protection, for example, by pivaloylation 3.) secondary alcohol protection, for example, by triethylsilylation 4.) primary alcohol deprotection, for example, by reduction with diisobutylaluminum hydride 5.) alcohol activation, for example, by treatment with trifluoroacetic anhydride in a solvent such as methylene chloride in the presence of a base such as pyridine. Numerous methods for alcohol protection and deprotection are described in "Protective Groups in Organic Synthesis" by T. W. Greene, John Wiley & Sons, Inc., 1981. In the case where X is p-toluenesulfonate, protection and deprotection of the primary alcohol (steps 2 and 4 above) are not necessary provided alcohol activation is performed prior to secondary alcohol protection. These compounds of formula III" where A is a bond may also be prepared from mandelic acids as exemplified by the preparation of 3-chloro-β-[[(1,1-dimethylethyl)dimethylsilyl]oxy]benzeneethanol, (trifluoromethyl)sulfonate described in U.S. Pat. No. 5,321,036, incorporated by reference herein.

The compound of formula VII where X is chlorine and $R^7$ is —$PO_3Et_2$ is commercially available. Compounds of formula VII where $R^7$ is —$SO_3H$ are prepared by the method described in R. B. Petigara et al., *J. Het. Chem.*, 11, 331 (1974). Compounds of formula VII where $R^7$ is —$P(O_2R^{7A})R^5$, are prepared as described in German patent application DE 2226406 and U.S. Pat. No. 4,536,355. Standard modifications of the described procedures that provide these compounds of formula VII where X is —$OSO_2Me$ enable the preparation of these compounds of formula VII where X is —$OSO_2CF$ and —$OSO_2C_6H_4CH_3$. The compounds of formula VII where $R^7$ is —$PO_3(R^{7A})_2$ and X is an oxygen atom leaving group, are prepared from the dialkyl or dibenzyl phosphite $(R^{7A}O)_2POH$ by first heating with triethylamine and paraformaldehyde or aqueous formaldehyde to generate $HOCH_2PO_3(R^{7A})_2$ and then activation of the hydroxyl for example by treatment with triflic anhydride, methanesulfonyl chloride, p-chlorobenzenesulfonyl chloride or p-toluenesulfonyl chloride in the presence of a base such as triethylamine, diisopropylethylamine or pyridine in a solvent such as methylene chloride or diethyl ether. See, for example, J. Comforth et al., *J. Chem. Soc. Perkin Trans I*, 1897 (1994).

In any of the above reactions, it may be necessary to protect certain substituents by using protecting groups as known by those skilled in the art.

Preferred compounds of formula I are those where the —O—$CH_2$—$R^4$ group is attached to the aromatic ring in the para or meta position relative to linker B.

The most preferred compounds of formula I are those where: $R^4$ is —$SO_3H$, —$P(O_2H)R^5$, or —$P(O_2R^{5'})R^5$.

The present compounds of formula I have activity at the beta 3 adrenergic receptor and are therefore useful, for example, in the treatment of diabetes, obesity, achalasia and gastrointestinal diseases such as inflammatory bowel disease, irritable bowel syndrome, nonspecific diarrhea, and peptic ulcer.

Thus a composition containing one (or a combination) of the compounds of this invention, may be administered to a species of mammal (e.g., humans) suffering from diabetes, obesity, achalasia or an intestinal hypermotility disorder as treatment therefor.

A single dose, or two to four divided daily doses, provided on a basis of about 0.1 to 100 mg per kilogram of body weight per day, preferably about 1 to 15 mg per kilogram of body weight per day is appropriate. The substance is preferably administered orally, but intranasal, transdermal and parenteral routes such as the subcutaneous, intramuscular, intravenous or intraperitoneal routes can also be employed.

The compounds of this invention can also be formulated in combination with $beta_1$/$beta_2$ adrenergic blockers or stimulants.

The compounds of formula I can be formulated for use in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Based on the literature, it is expected that these compounds may be useful for other indications such as treatment of depression and stress, regulation of intraocular pressure, treatment of conditions associated with increased protein breakdown such as during convalescence after surgery, treatment of hypertriglyceridemia, hypercholesterolemia, atherosclerotic and cardiovascular diseases, and increasing high density lipoprotein levels. In addition, it is expected that these compounds may be useful as feed additives for fattening or improving weight gain or increasing lean body mass in animals and may therefore be used to decrease birth mortality and increase post-natal survival rates in animals.

The following examples and preparations describe the manner and process of making and using the invention and are illustrative rather than limiting. It should be understood that there may be other embodiments which fall within the spirit and scope of the invention as defined by the claims appended hereto.

Example 1

[R-(R*,R*)]-[4-[2-[[2-(3-Chlorophenyl)-2-hydroxyethyl]amino]propyl]phenoxy]methanesulfonic acid, monosodium salt

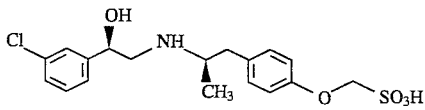

A. (3-Chlorophenyl)oxirane

Prepared from 3-chlorostyrene by the method described in M. Imuta et at., *J. Org. Chem.*, 44, 1351 (1979).

B. (R)-4-Methoxy-α-methylbenzeneethanamine

Prepared as described in D. E. Nichols et al., *J. Med. Chem.*, 16, 480 (1973). The ee of this amine was shown to be 99.8% based on chiral HPLC analysis against the enantiomer on an ES Industries C-18 BD column eluting with 53% of 25 mM aqueous $KH_2PO_4$ (pH 7) and 47% MeCN.

C. (1R)-3-Chloro-α-[[[2-(4-methoxyphenyl)-1-methylethyl]amino]methyl]benzenemethanol Amine/epoxide coupling mediated by TMS-acetamide are described in R. K. Atkins et al., *Tet. Lett.*, 27, 2451 (1986).

To the title B compound (m.w. 165, 2.92 g, 17.7 mmol) at room temperature under argon was added N-(trimethylsilyl)acetamide (m.w. 131, 2.41 g, 18.4 mmol, 1.04 equiv.). The resulting solution was stirred at room temperature for 90 minutes. To this was then added the title A compound (m.w. 154, 2.73 g, 17.7 mmol, 10 equiv.). The resulting solution was heated at 65°–70° C. for three days, then the temperature was increased to 80° C. After a total of six days, the reaction mixture was cooled to room temperature and diluted with ethyl acetate (~50 mL). About 150 mL of chipped ice and 3 mL conc. hydrochloric acid were added to the solution. This mixture was stirred for three hours, allowing the ice to melt. The mixture was basified to pH 12 by addition of 1M aq. sodium hydroxide. The ethyl acetate layer was removed, and the aqueous layer was then extracted three times with methylene chloride (100 mL). The various organic extracts were combined and dried over sodium sulfate, and then concentrated to a thick oil, which was purified by silica gel chromatography eluting with 7% (10% conc. aq. ammonium hydroxide/methanol)/methylene chloride. This produced the title compound as a yellow oil (5.10 g, 90% yield).

TLC: $R_f$=0.15 in 5% (10% conc. aq. ammonium hydroxide/methanol)/methylene chloride, p-anisaldehyde stain, UV.

D. [R-(R*,R*)]-5-(3-Chlorophenyl)-3-[2-(4-methoxyphenyl)-1-methylethyl]-2-oxazolidinone To a solution of the title C compound (m.w. 319, 5.10 g, 16.0 mmol) in $CDCl_3$ (~15 mL) at room temperature under argon was added triethylamine (m.w. 101, d 0.72, 3.4 mL, 2.4 g, 23.6 mmol, 1.5 equiv.) and 1,1'-carbonyldiimidazole (m.w. 162, 3.9 g, 24.1 mmol, 1.5 equiv.). The resulting solution was stirred overnight at room temperature, and then concentrated to an oil. The oil was chromatographed twice on silica gel eluting first with 2% (10% conc. aq. ammonium hydroxide/methanol)/methylene chloride and then with 30% ethyl acetate/hexane. The desired product was isolated as 1.7 g of 99% pure, clear, colorless oil, giving a 30% yield (50% is theoretical). The 1% impurity was identified by analytical HPLC as the undesired diastereomer. On a gradient of 0–100% B (A=90% water/10% methanol/0.2% phosphoric acid, B=10% water/90% methanol/0.2% phosphoric acid) over 40 minutes (YMC S3ODS (C18) 6.0×150 mm column) at a flow rate of 1.5 mL/minute, the desired diastereomer eluted at 36.2 minutes, and the undesired diastereomer eluted at 36.9 minutes. The methyl doublet in the proton NMR (270 MHz, $CDCl_3$) is at δ1.23 in the desired diastereomer and at δ1.20 in the undesired diastereomer. A multiplet appears at δ4.30 in the desired diastereomer and at δ4.20 in the undesired diastereomer. TLC of the title D compound: $R_f$=0.90 in 5% (10% conc. aq. ammonium hydroxide/methanol)/methylene chloride, p-anisaldehyde stain, UV. TLC of the undesired diastereomer: $R_f$=0.92 in 5% (10% conc. aq. ammonium hydroxide/methanol)methylene chloride, p-anisaldehyde stain, UV.

$^{13}C$ NMR (67.7 MHz in $CDCl_3$): δ17.7, 39.3, 47.8, 49.9, 55.1, 73.4, 113.9, 123.5, 125.6, 128.7, 129.3, 129.8, 130.1, 134.7, 141.2, 156.9, 158.3.

E. [R-(R*,R*)]-5-(3-Chlorophenyl)-3-[2-(4-hydroxyphenyl)-1-methylethyl]-2-oxazolidinone To a solution of the title D compound (1.7 g, m.w. 345, 4.9 mmol) in methylene chloride at 0° C. under argon was added $BBr_3$ (1.0M in methylene chloride, 14.8 mL, 3.0 equiv.). The solution was stirred at 0° C. for 30 minutes and then quenched by careful addition of water (50 mL). The organic layer was removed, and the aqueous layer was then extracted five times methylene chloride (50 mL). The combined organic extracts were dried (sodium sulfate) and then concentrated to give the title compound as a tan foam (1.5 g, 94% yield).

TLC: $R_f$=0.5 in 5% (10% conc. aq. ammonium hydroxide/methanol)methylene chloride, p-anisaldehyde stain, UV.

$^{13}C$ NMR (67.7 MHz in $CDCl_3$): δ17.7, 39.0, 47.3, 49.7, 73.8, 115.4, 123.5, 125.6, 128.1, 128.6, 129.5, 130.2, 134.2, 140.5, 155.2, 157.6.

F. [R-(R*,R*)]-[4-[2-[5-(3-Chlorophenyl)-2-oxo-3-oxazolidinyl] propyl]phenoxy]methanesulfonic acid, monosodium salt To a solution of the title E compound (m.w. 331, 500 mg, 1.52 mmol) and sodium bromomethylsulfonate (R. B. Petigara et al., *J. Het. Chem.*, 11, 331 (1974), m.w. 197, 300 mg, 1.52 mmol, 1.0 equiv.) in water (4–5 mL) was added sodium hydroxide (1.0M aq., 1.52 mL, 1.52 mmol. 1.0 equiv.). The pH of the solution at this point was 9. The solution was lyophilized to obtain a powder, which was then heated neat at 200° C. for one hour under argon. The melt was cooled to room temperature and then dissolved in water (40 mL). The pH of the solution was lowered to 3 by addition of 1M aq. hydrochloric acid. The solution was washed three times with ether (40 mL). The aqueous layer was then concentrated to a total volume of ~10 mL and purified on a Waters Sep-Pak cartridge (C-18, 5 g) eluting with 0–100% methanol/water.

The clean fractions were combined and lyophilized to give the title compound as a white lyophilate (240 mg, >35% yield).

$^{13}$C NMR (67.7 MHz in CD$_3$OD): δ18.1, 39.7, 51.1, 54.8, 75.1, 80.0, 116.4, 124.9, 126.4, 129.7, 130.8, 131.6, 132.4, 135.4, 142.9, 158.1.

G. [R-(R*,R*)]-[4-[2-[[2-(3-Chlorophenyl)-2-hydroxyethyl] amino]propyl]phenoxy]methanesulfonic acid, monosodium salt A solution of the title F compound (m.w. 447, 240 mg, 0.54 mmol) in ~4 mL aq. sodium hydroxide (5M) was heated at reflux for 18 hours under argon. The product was purified on a Sep-Pak cartridge (C-18, 5 g), eluting with 0–20% methanol/water. The cleanest fractions were lyophilized to give the tire compound as a white lyophilate (150 mg, >66% yield).

MS: (M(Na)+H)$^+$ at 422.

Example 2

[[4-[(R)-2-[[2-(3-Chlorophenyl)-2-hydroxyethyl]amino] propyl]phenoxy]methyl]phosphonic acid, disodium salt

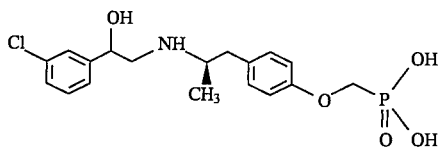

A. (αR)-N-[2-(3-Chlorophenyl)-2-[[(1,1-dimethylethyl)dimethylsilyl] oxy]ethyl]-4-methoxy-α-methylbenzeneethanamine To a solution of the Example 1B compound (1.65 g, 10.0 mmol) in dry CH$_3$CN (~15 mL) at room temperature under argon was added diisopropylethylamine (1.29 g, 10.0 mmol) followed by 3-chloro-β-[[(1,1-dimethylethyl)-dimethylsilyl] oxy]benzeneethanol, (trifluoromethyl)sulfonate (4.19 g, 10.0 mmol; prepared as described in U.S. Pat. No. 5,321, 036). The resulting solution was stirred overnight at room temperature, and then concentrated to an oil. The crude product was used as such in the next step.

TLC: R$_f$=0.42 in 50% ethyl acetate/hexane, UV; PMA.

B. (αR)-N-[2-(3-Chlorophenyl)-2-hydroxyethyl] -4-methoxy-α-methylbenzeneethanamine To a solution of all of the crude title A compound in dry tetrahydrofuran (~15 mL) at room temperature under argon was added a 1.0M solution of TBAF in THF (30 mL) and the resulting solution was stirred at room temperature for four hours and then concentrated to an oil. The crude oil was purified by silica gel chromatography eluting with 0% to 7% (10% conc. aq. ammonium hydroxide/methanol)/methylene chloride. This produced 3.9 g of impure title B compound.

C. (1R)-5-(3-Chlorophenyl)-3-[2-(4-methoxyphenyl)-1-methylethyl]- 2-oxazolidinone The title C compound was prepared from the title B compound by the same procedures as those described for the preparation of the Example 1D compound, except that the diastereomers were not separated.

D. (1R)-5-(3-Chlorophenyl)-3-[2-(4-hydroxyphenyl)- 1-methylethyl]-2-oxazolidinone The title D compound was prepared from the title C compound by the same procedures as those described for the preparation of the Example 1E compound.

E. Diisopropyl trifluoromethanesulfonyloxymethylphosphonate

1. Diisopropyl hydroxymethylphosphonate

A mixture of 33.2 g (0.20 mol) of diisopropyl phosphite, 2.8 mL (0.02 mol) of triethylamine, and 6.0 g (0.20 mol) of paraformaldehyde, was immersed in a 100° C. oil bath and then heated between 100°–120° C. for 45 minutes under nitrogen. An exotherm occurred within 10 minutes, and all of the paraformaldehyde dissolved rapidly. The triethylamine was removed at reduced pressure, and the residue was bulb-to-bulb distilled in four portions to provide a total of 35.17 g (90%) of the title compound as a colorless oil.

TLC: Silica gel (5:95 methanol:methylene chloride) R$_f$=0.17.

2. Diisopropyl trifluoromethanesulfonyloxymethylphosphonate

To a stirred solution of 6.0 g (30.6 mmol) of the title 1 compound in 100 mL of dry ether at –78° C. was added 5.90 mL (33.9 mmol) of diisopropylethylamine followed by the addition of 5.20 mL (31.0 mmol) of trifluoromethanesulfonic anhydride in 10 mL of ether over 30 minutes. An additional 40 mL of ether was added to aid stirring through the thick precipitate. After 45 minutes at –78° C., the reaction mixture was allowed to warm to 0° C. for 45 minutes, and the solids were filtered and rinsed with ether. The filtrate was evaporated to afford 9.4 g of a colorless liquid. The crude product was flash chromatographed on 150 g of silica gel eluted with 40:60 ethyl acetate:hexane to provide 5.7 g (57%) of pure title E compound as a colorless liquid.

TLC: Silica gel (50:50 ethyl acetate:hexane) R$_f$=0.34.

F. [[4-[(R)-2-[5-(3-Chlorophenyl)-2-oxo-3-oxazolidinyl] -propyl]phenoxy]methyl]phosphonic acid, bis(1-methylethyl)ester To a stirring solution of the title D compound (m.w. 332, 330 mg, 0.99 mmol) in 5 mL of dry tetrahydrofuran under argon at 0° C. was added 60% sodium hydride oil dispersion (50 mg, 30 mg net, 1.25 mmol). After 30 minutes a solution of the title E compound (407 mg, 1.24 mmol) in dry tetrahydrofuran (4–5 mL) was added via a cannula. The mixture was stirred at 0° C. for 30 minutes and then warmed to room temperature and stirred overnight. 5 mL of water was added and the mixture was extracted with 20 mL of ethyl acetate. The organic phase was washed with brine and dried over anhydrous sodium sulfate. Removal of the solvent under reduced pressure gave the crude title compound as a mixture of two diastereomers.

HPLC on a gradient of 0–100% B (A=90% water/10% MeOH/0.2% phosphoric acid, B=10% water/90% MeOH/ 0.2% phosphoric acid) over 45 minutes (YMC S3ODS (C18) 6.0×150 mm column) at a flow rate of 1.5 mL/minute retention times 41.5 minutes and 42.3 minutes. TLC: R$_f$'s= 0.21 and 0.29 in 50% ethyl acetate/hexane, UV.

G. [[4-[(R)-2-[[2-(3-Chlorophenyl)-2-hydroxyethyl] amino] propyl]phenoxy]methyl]phosphonic acid, disodium salt To a solution of all of the crude title F compound (prepared in step F) in 2 mL of methylene chloride at room temperature under argon was added allyltrimethylsilane (164 μL, 118 mg, 1.04 mmol) and bromotrimethylsilane (681 μL, 790 mg, 5.16 mmol). The reaction mixture was stirred at room temperature for four hours. Solvent and volatiles were removed under reduced pressure to yield a light brown oil which was dissolved in ethanol (~24 mL). 13 mL of aq. sodium hydroxide (5M) was added and the mixture was stirred under argon at reflux for four hours. After cooling to room temperature the solvent was removed under reduced pressure. The product was purified by preparative HPLC on an ODS (C18) column eluted with 40% methanol/water. The cleanest fractions were lyophilized to give the title compound as 90 mg of white lyophilate.

MS: (M(H$_2$)+H)$^+$ at 400, (M(H$_2$)+Na)$^+$ at 422, (M(Na$_2$)+H)$^+$ at 444, (M(Na$_2$)+Na)$^+$ at 466.

HPLC on a gradient of 0–100% B (A=90% water/10% MeOH/0.2% phosphoric acid. B=10% water/90% MeOH/0.2% phosphoric acid) over 45 minutes (YMC S3ODS (C18) 6.0×150 mm column) at a flow rate of 1.5 mL/minutes retention time 20.8 minutes. The intermediate oxazolidinone phosphonic acid diastereomers eluted at 30.0 and 33.0 minutes.

Example 3

[4-[(R)-2-[[2-(3-Chlorophenyl)-2-hydroxyethyl]amino]propyl]phenoxy]methyl]phosphonic acid, 1-methylethyl ester, monosodium salt

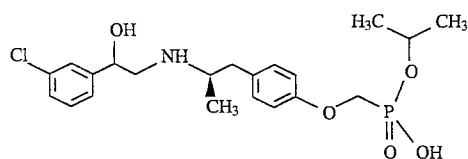

To a solution of the Example 2F compound (200 mg, 0.39 mmol) in 5 mL of ethanol was added ~4 mL aq. sodium hydroxide (5M). This mixture was stirred under argon at reflux for six hours, then cooled to room temperature, and the solvent was removed under reduced pressure. The product was purified by preparative HPLC on an ODS (C18) column eluted with 49% methanol/water. The cleanest fractions were lyophilized to give the title compound as 120 mg of white lyophilate.

MS: $(M(H)+H)^+$ at 442, $(M(Na)+H)^+$ at 464, $(M(Na)+Na)^+$ at 486.

HPLC on a gradient of 0–100% B (A=90% water/10% MeOH/0.2% phosphoric acid, B=10% water/90% MeOH/0.2% phosphoric acid) over 45 minutes (YMC S3ODS (C18) 6.0×150 mm column) at a flow rate of 1.5 mL/minute retention time 29.5 minutes.

What is claimed is:

1. A compound of the formula

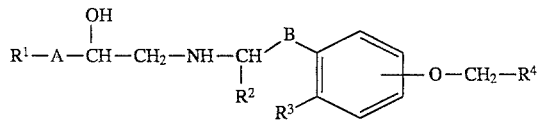

or pharmaceutically acceptable salts thereof wherein:

A is a bond or $-OCH_2-$, where the oxygen is linked to $R^1$;

B is $-CH_2-$ or when $R^3$ is hydrogen, B may be $-CH_2O-$ where the oxygen is linked to the phenyl ring;

$R^1$ is an aryl group;

$R^2$ is hydrogen or lower alkyl;

$R^3$ is hydrogen; or $R^2$ and $R^3$ together form the group $-CH_2CH_2-$; and $R^4$ is $-SO_3H$, $-P(O_2H)R^5$, $-P(O_2R^{5'})R^5$, $-PO_3H_2$, $-PO_3HR^{5'}$ or $-PO_3(R^{5'})_2$ where $R^5$ and $R^{5'}$ are independently lower alkyl; provided that when A is a bond, $R^4$ is other than $-PO_3H_2$, $-PO_3HR^{5'}$, or $-PO_3(R^{5'})_2$.

2. The compounds as recited in claim 1 wherein the $-O-CH_2-R^4$ group is attached to the aromatic ring in the para or meta position relative to B.

3. A compound of the formula

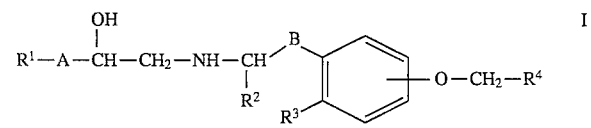

or pharmaceutically acceptable salts thereof wherein:

A is a bond or $-OCH_2-$, where the oxygen is linked to $R^1$;

B is $-CH_2-$ or when $R^3$ is hydrogen, B may be $-CH_2O-$ where the oxygen is linked to the phenyl ring;

$R^1$ is an aryl group;

$R^2$ is hydrogen or lower alkyl;

$R^3$ is hydrogen; or $R^2$ and $R^3$ together form the group $-CH_2CH_2-$; and $R^4$ is $-SO_3H$, $-P(O_2H)R^5$ or $-P(O_2R^{5'})R^5$ where $R^5$ and $R^{5'}$ are independently lower alkyl.

4. The compound as recited in claim 3, which is [R-(R*,R*)]-[4-[2-[[2-(3-chlorophenyl)- 2-hydroxyethyl]amino] propyl]phenoxy]methanesulfonic acid, monosodium salt.

5. A pharmaceutical composition comprising a compound of claim 1 and a pharmaceutically acceptable carrier.

6. A method for treating diabetes comprising administering to a mammalian specie in need thereof a therapeutically effective amount of a composition of claim 5.

7. A method for treating obesity comprising administering to a mammalian specie in need thereof a therapeutically effective amount of a composition of claim 5.

8. A method for treating achalasia comprising administering to a mammalian specie in need thereof a therapeutically effective amount of a composition of claim 5.

9. A method for treating intestinal hypermotility comprising administering to a mammalian specie in need thereof a therapeutically effective amount of a composition of claim 5.

10. A pharmaceutical composition comprising a compound of claim 1 in combination with a beta$_1$ or beta$_2$ adrenergic blocker or stimulant and a pharmaceutically acceptable carrier.

11. A method for treating diabetes comprising administering to a mammalian specie in need thereof a therapeutically effective amount of a composition of claim 10.

12. A method for treating obesity comprising administering to a mammalian specie in need thereof a therapeutically effective amount of a composition of claim 10.

13. A method for treating achalasia comprising administering to a mammalian specie in need thereof a therapeutically effective amount of a composition of claim 10.

14. A method for treating gastrointestinal diseases comprising administering to a mammalian specie in need thereof a therapeutically effective amount of a composition of claim 10.

* * * * *